United States Patent [19]

Miyashita

[11] Patent Number: 4,772,432
[45] Date of Patent: Sep. 20, 1988

[54] 7,7,8,8,TETRACYANOQUINODIMETHANE-2,5-YLENE-(3-PROPIONIC ACID) AND DERIVATIVES THEREOF

[75] Inventor: Masahiko Miyashita, Osaka, Japan

[73] Assignee: Nippon Gosei Kagaku Kogyo Kabushiki Kaisha, Japan

[21] Appl. No.: 878,199

[22] Filed: Jun. 25, 1986

[30] Foreign Application Priority Data

Jul. 27, 1985 [JP]  Japan ................................ 60-166081

[51] Int. Cl.$^4$ ............................................ C07C 121/48
[52] U.S. Cl. ................................ 260/396 N; 558/430; 560/126; 562/508
[58] Field of Search ..................................... 260/396 N

[56] References Cited

U.S. PATENT DOCUMENTS 3,115,506 12/1963 Acker et al. ................... 260/396 N
3,526,497  9/1970 Obreiter et al. ............... 260/396 N
4,229,364 10/1980 Crawford ....................... 260/396 N Primary Examiner—Vivian Garner
Attorney, Agent, or Firm—McGlew and Tuttle

[57] ABSTRACT 7,7,8,8-Tetracyanoquinodimethane-2,5-ylene-(3-propionic acid) and derivatives thereof represented by the formula

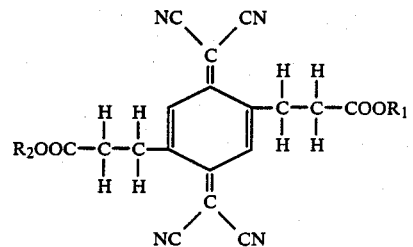

wherein $R_1$ and $R_2$ are each hydrogen or alkyl. The compounds are useful as materials for preparing polyesters, polyamides and polyurethanes or as intermediates for tetracyanoquinodimethanes for use as organic semiconductors.

3 Claims, No Drawings

7,7,8,8,TETRACYANOQUINODIMETHANE-2,5-YLENE-(3-PROPIONIC ACID) AND DERIVATIVES THEREOF

BACKGROUND OF THE INVENTION

1. Field of the Invention

The present invention relates to novel compounds which are useful as materials for producing polyesters, polyamides, polyurethanes, etc. or as intermediates for tetracyanoquinodimethanes which are expectedly useful as organic semiconductors.

2. Description of the Prior Art 7,7,8,8-Tetracyanoquinodimethane is in the form of yellow crystals melting at 293.5° to 296° C. This compound readily accepts one electron to form a stable anionic radical, and derivatives thereof exhibit very low electric resistance. When reduced with thiophenol, mercaptoacetic acid, hydrogen iodide or the like, the compound is converted to phenylenedimalononitrile, which returns to 7,7,8,8-tetracyanoquinodimethane when oxidized with N-chlorosuccinimide.

It is known to prepare 7,7,8,8-tetracyanoquinodimethane, for example, by subjecting malononitrile and 1,4-cyclohexane-dione to a condensation reaction to obtain 1,4-bis(dicyanomethylene)cyclohexane, and oxidizing the cyclohexane in pyridine with N-bromosuccinimide or bromine.

7,7,8,8-Tetracyanoquinodimethane, although an organic compound, is electrically conductive as already mentioned, so that it is useful to find other processes for preparing the compound or to find electrically conductive compounds resembling the compound in skeleton. Such attempts will be important to the research on and development and application of conductive organic compounds of this type.

Since 7,7,8,8-tetracyanoquinodimethane has a very high melting point as mentioned above and is almost insoluble in organic solvents, these properties are limiting factors to the use of the compound. Accordingly, it is of importance to find analogous compounds free of such drawbacks.

SUMMARY OF THE INVENTION

We have carried out intensive research to overcome the foregoing problem and accomplished the present invention.

The present invention provides 7,7,8,8-tetracyanoquinodimethane-2,5-ylene-(3-propionic acid) and derivatives thereof represented by the formula

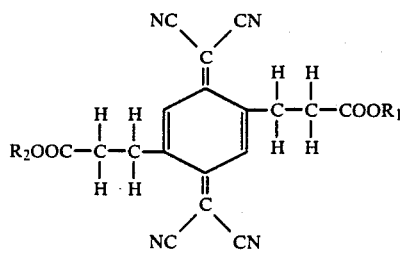

wherein $R_1$ and $R_2$ are each hydrogen or alkyl. These compounds are novel compounds not disclosed in literature.

The present invention further provides a process for preparing the compounds of the formula (I).

DETAILED DESCRIPTION OF THE INVENTION

The compounds of the present invention are represented by the formula (I). Examples of alkyl groups are those having 1 to about 10 carbon atoms, such as methyl, ethyl, propyl, butyl, amyl, hexyl, octyl, decyl, cyclohexyl, etc. Important from an industrial viewpoint are lower alkyl groups having 1 to about 4 carbon atoms, especially methyl.

When both $R_1$ and $R_2$ in the formula (I) are methyl, the compound of the present invention has a melting point of as low as 168° C. and is satisfactorily soluble in common solvents such as methanol. The compound therefore has the advantage of being usable for wider applications.

The process for preparing the compounds of the present invention will be described below.

The compound of the invention is prepared by oxidizing 2,5-bis(dicyanomethylene)cyclohexane-1,4-ylene(3-propionic acid) or a derivative thereof represented by the formula

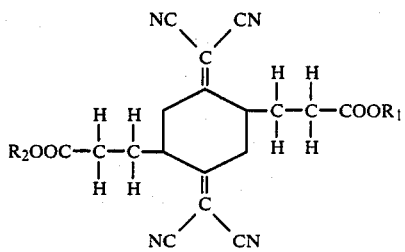

wherein $R_1$ and $R_2$ are each hydrogen or alkyl.

The oxidation reaction is conducted in an inert gas atmosphere using N-bromosuccinimide or bromine, usually in acetonitrile or other medium in the presence of pyridine or other basic substance.

Satisfactory results can be achieved when the reaction is carried out at 0° to 80° C. for 0.1 to 8 hours.

N-Bromosuccinimide or bromine is reacted with 2,5-bis(dicyanomethylene)cyclohexane-1,4-ylene-(3-propionic acid) or a derivative thereof represented by the formula (II) usually in the ratio of 1 to 5 moles of the former per mole of the latter.

After the completion of the reaction, water is added to the reaction mixture as required to separate out a precipitate, which is then purified by the usual method.

When 2,5-bis(dicyanomethylene)cyclohexane-1,4-ylene-(3-propionic acid) of the formula (II) is used as the starting material, 7,7,8,8-tetracyanoquinodimethane-2,5-ylene-(3-propionic acid) is obtained. When the starting material used is an alkyl ester of 2,5-bis(dicyanomethylene)cyclohexane-1,4-ylene-(3-propionic acid) of the formula (II), the reaction affords the corresponding alkyl ester of 7,7,8,8-tetracyanoquinodimethane-2,5-ylene-(3-propionic acid).

In the former case, the product, when esterified, gives the latter product. The esterification is conducted by a known method, for example, by converting the former product to an acid chloride with thionyl chloride or the like and reacting the resulting product with an alcohol. The esterification can be effected also during the oxidation reaction by carrying out the oxidation reaction in the presence of an alcohol.

2,5-Bis(dicyanomethylene)cyclohexane-1,4-ylene(3-propionic acid) or an ester thereof represented by the formula (II) and serving as the starting material can be prepared, for example, by the following process. A dialkyl ester of succinylsuccinic acid represented by the formula

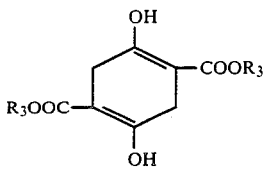

wherein R₃ is alkyl is reacted with acrylic acid alkyl ester of acrylic acid represented by the formula

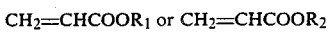

CH₂=CHCOOR₁ or CH₂=CHCOOR₂ wherein R₁ and R₂ are each hydrogen or alkyl to obtain a cyclohexane-2,5-dione derivative represented by the formula

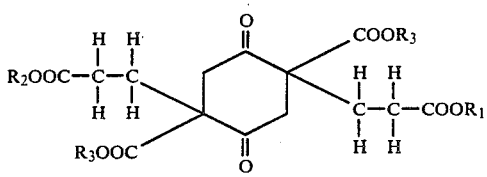

wherein R₁, R₂ and R₃ are as defined above. The reaction is conducted usually in an organic solvent in the presence of a metallic alcoholate catalyst.

The cyclohexane-2,5-dione derivative is then heated in an aqueous medium in the presence of a strong acid, such as hydrochloric acid, sulfuric acid, p-toluenesulfonic acid or a strong-acid type ion exchange resin, to give cyclohexane-2,5-dione-1,4-ylene-(3-propionic acid) represented by the formula

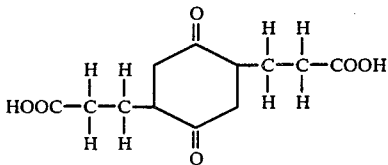

When esterified, the product affords an ester of cyclohexane-2,5-dione-1,4-ylene-(3-propionic acid).

Subsequently, the cyclohexane-2,5-dione-1,4-ylene-(3-propionic acid) or the ester thereof is reacted with malondinitrile, giving 2,5-bis(dicyanomethylene)cyclohexane-1,4-ylene-(3-propionic acid) or an ester thereof useful as the starting material of the invention.

It is expected that the compounds of the present invention will find various uses. For example, the present compounds are useful as materials for producing polyesters, polyamides, polyurethanes, etc. and as intermediates for tetracyanoquinodimethane serving as organic semiconductors.

Polyesters can be produced by subjecting the compound of the present invention, a polycarboxylic acid, such as phthalic acid, isophthalic acid, maleic acid or maleic anhydride, and a polyhydric alcohol, such as ethylene glycol or propylene glycol, to a condensation reaction. Polyamides can be prepared by subjecting the present compound, a polycarboxylic acid such as adipic acid and a polyamine compound such as ethylenediamine to a condensation reaction. Polyurethanes can be prepared by reacting the present compound with a polyhydric alcohol such as ethylene glycol and a polyisocyanate compound such as tolylene diisocyanate.

The present invention will be described in greater detail with reference to the following examples.

EXAMPLE 1

Preparation of cyclohexane-2,5-dione derivative

A 128.13 g quantity (0.5 mole) of diethyl succinylsuccinate, 112.4 g (1.0 mole) of methyl acrylate, 2.18 g (0.04 mole) of sodium methylate and 700 ml of methanol were mixed together in a reactor, the air within the reactor was replaced by argon, and the mixture was reacted for 15 hours with refluxing. The methanol was then distilled off at a reduced pressure, and a small amount of water containing benzene was added to the residue. The benzene layer was separated off, dried and then distilled in a vacuum, giving 181.97 g of yellowish brown oil.

Preparation of cyclohexane-2,5-dione-1,4-ylene(3-propionic acid)

A 177.55 g (0.414 mole) portion of the oil (cyclohexane-2,5-dione derivative) thus obtained, 300 ml of water and 10 g of concentrated sulfuric acid were mixed together. The mixture was reacted with refluxing for 120 hours while distilling off the resulting methanol and ethanol from time to time. The reaction mixture was thereafter cooled.

The crystals separating out were filtered off, giving 29.98 g of a product melting at 190° C. The product was recrystallized from water, affording cyclohexane-2,5-dione-1,4-ylene-(3-propionic acid), m.p. 192° to 194° C.

Preparation of 2,5-bis(dicyanomethylene)cyclohexane-1,4-ylene-(3-propionic acid)

A 1.28 g (5 mmoles) quantity of the cyclohexane2,5-dione-1,4-ylene-(3-propionic acid) thus prepared was dissolved in 30 ml of water and then neutralized with an equivalent of sodium hydrogencarbonate. With addition of 0.66 g (10 mmoles) of malondinitrile and 0.1 g of β-alanine, the mixture was heated in a water bath for 2 hours, cooled and thereafter acidified with dilute hydrochloric acid. The crystals separating out were filtered off, washed and dried, giving 0.86 g of 2,5-bis(dicyanomethylene)cyclohexane-1,4-ylene-(3-propionic acid).

Preparation of methyl 2,5-bis(dicyanomethylene)cyclohexane1,4-ylene-(3-propionic acid)

The 0.86 g quantity of 2,5-bis(dicyanomethylene)cyclohexane-1,4-ylene-(3-propionic acid) obtained was dissolved in methanol. The solution was stirred at 10° C. for 2 hours with addition of 3.1 g of thionyl chloride. The resulting crystals were filtered off, washed and dried, giving 0.83 g of 2,5-bis(dicyanomethylene)cyclohexane-1,4-ylene-(3-propionic acid) methyl ester.

Preparation of compound of the invention

A 0.57 g quantity of the methyl ester of 2,5-bis(dicyanomethylene)-cyclohexane-1,4-ylene-(3-propionic acid) obtained was suspended in 50 ml of acetonitrile. In an argon atmosphere, the suspension was stirred for 1 hour with addition of 0.6 g of N-bromosuccinimide. The mixture was cooled and then stirred for 2 hours with addition of 0.9 g of pyridine while maintaining the mixture at a temperature of up to 10° C. Water (30 ml) was added to the reaction mixture. The precipitate separating out was filtered off, washed with water and dried to obtain 0.51 g of the desired product. The yield was 90% based on the 2,5-bis(dicyanomethylene)cyclohexane-1,4-ylene(3-propionic acid) methyl ester.

The compound had the following characteristics values and was identified as methyl ester of 7,7,8,8-tetracyanoquinodimethane-2,5-ylene-(3-propionic acid).

| M.p. | 167–168° C. |
|---|---|
| IR $\nu_{KBr}^{cm^{-1}}$ | 3050, 2960, 2215, 1740, 1550, 1515, 1200 1175, 915, 900 |
| NMR $\delta_{CDCl_3}^{ppm}$—DMSO | 2.81 (4H T), 3.66 (6H S) |
| Mass m/e | 376, 345, 344, 317, 303, 259, 258(B), 257 |

EXAMPLE 2

7,7,8,8-Tetracyanoquinodimethane-2,5-ylene(3-propionic acid) was obtained in a yield of 80% in the same manner as in Example 1 except that 2,5-bis(dicyanomethylene)cyclohexane-1,4-ylene-(3-propionic acid) was used in place of the methyl ester of 2,5-bis(dicyanomethylene)cyclohexane-1,4-ylene-(3-propionic acid).

EXAMPLES 3-4

Ethyl ester or n-propyl ester of 7,7,8,8-tetracyanoquinodimethane-2,5-ylene-(3-propionic acid) was prepared in the same manner as in Example 1 with the exception of using ethyl ester or n-butyl ester of 2,5-bis(dicyanomethylene)cyclohexane-1,4-ylene-(3-propionic acid) in place of the methyl ester thereof.

ADVANTAGE OF THE INVENTION

The present invention provides 7,7,8,8-tetracyanoquinodimethane-2,5-ylene-(3-propionic acid) and esters thereof which are novel compounds. Accordingly, materials for producing polyesters, polyamides, polyurethanes, etc. and intermediates for tetraquinodimethanes serving as organic semiconductors can be prepared via the route provided by the invention other than the conventional methods.

What is claimed is:

1. 7,7,8,8-tetracyanoquinodimethane-2,5-ylene-(3-propionic acid) or a deriviative thereof represented by the formula

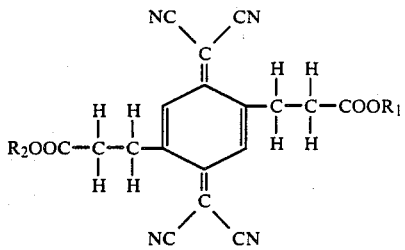

wherein $R_1$ and $R_2$ are each hydrogen or alkyl.

2. A 7,7,8,8-tetracyanoquinodimethane-2,5-ylene-(3-propionic acid) derivative as defined in claim 1 which is represented by the formula (I) wherein $R_1$ and $R_2$ are each alkyl having 1 to 10 carbon atoms.

3. 7,7,8,8-tetracyanoquinodimethane-2,5-ylene-(3-propionic acid) derivative as defined in claim 1 which is represented by the formula (I) wherein $R_1$ and $R_2$ are each methyl.

* * * * *